United States Patent [19]

Maruyama

[11] 4,394,502

[45] * Jul. 19, 1983

[54] IMMUNOTHERAPEUTIC AGENT FOR TUMORS COMPRISING LIPOPOLYSACCHARIDE AS AN ACTIVE COMPONENT

[76] Inventor: Chisato Maruyama, No. 20-6, 1-chome, Mukogaoka, Bunkyo-ku, Tokyo-to, Japan

[*] Notice: The portion of the term of this patent subsequent to May 11, 1999, has been disclaimed.

[21] Appl. No.: 293,999

[22] Filed: Aug. 18, 1981

Related U.S. Application Data

[63] Continuation-in-part of Ser. No. 147,127, May 6, 1980, Pat. No. 4,329,452.

[30] Foreign Application Priority Data

Jul. 4, 1979 [JP] Japan ................................ 54-84681

[51] Int. Cl.³ ...................... C08B 37/00; A61K 31/72; C07H 13/02
[52] U.S. Cl. .................................... 536/119; 424/88; 424/92; 424/180
[58] Field of Search ............... 424/88, 92, 180; 536/1, 536/4, 119

[56] References Cited

U.S. PATENT DOCUMENTS 3,600,378  8/1971  Marsh et al. .......................... 424/92
3,956,481  5/1976  Jolles et al. .......................... 424/92

OTHER PUBLICATIONS

Chemical Abstracts, vol. 84, p. 271, Abst. No. 147295t, 1976.
Biological Abstracts, vol. 54, p. 4766, Abst. No. 49265, 1972.

*Primary Examiner*—Blondel Hazel
*Attorney, Agent, or Firm*—Scrivener, Clarke, Scrivener and Johnson

[57] ABSTRACT

Disclosed is a novel immunotherapeutic agent for tumors, which comprises as an active component a lipopolysaccharide derived from human tubercle bacillus or a lipopolysaccharide formed by chemically modifying said lipopolysaccharide.

5 Claims, No Drawings

IMMUNOTHERAPEUTIC AGENT FOR TUMORS COMPRISING LIPOPOLYSACCHARIDE AS AN ACTIVE COMPONENT

CROSS REFERENCE TO CO-PENDING APPLICATION

This application is a continuation-in-part of U.S. application Ser. No. 147,127, filed May 6, 1980 now U.S. Pat. No. 4,329,452.

BACKGROUND OF THE INVENTION

The present invention relates to a novel immunotherapeutic agent for tumors.

Recently, attempts have been extensively made to extract components effective for remedy of cancer from cell body of various bacteria and bacterial products. Particularly, trials have been vigorously made to obtain carcinostatic agents with less toxicity by extracting components having carcinostatic activity from cell body of mycobacteria.

Furthermore, clinical researches for remedy of cancer have been vigorously made by using components of BCG cell body or cell body of other mycobacteria as immunotherapeutic agents for various cancers of animals. However, BCG cell body contains components causing side effects as well as effective components, and increase in administration of the cell body per se is very dangerous. Therefore, it has been desired to develop immunotherapeutic agents by removing components causing side effects from the cell body and selectively extracting effective components alone or promoting the activity of effective components by some treatment or other. Thus, there have been developed a cellular wall skeleton component of BCG (see Japanese Patent Application laid open to public under No. 28813/1979), muramyl dipeptide (See Japanese Patent Application laid open to public under Nos. 156812/1977 and 98922/1978), and a glycolipid containing long-chain fatty acid in waxy substance D (See Japanese Patent Application laid open to public under Nos. 3514/1978 and 28830/1979).

It is a primary object of the present invention to provide an effective immunotherapeutic agent for tumors.

Another object of the present invention is to provide an immunotherapeutic agent for tumors which has no side effect.

The inventor found that when the young and weak cell body of human tubercle bacillus, Mycobacterium tuberculosis strain Aoyama B, or Mycobacterium tuberculosis strain $H_{37}R_v$, is extracted with hot water and the recovered lipopolysaccharide component is purified by fractional purification, lipoarabinomannan having antitumor activity and no side effect can be obtained. The inventor further found that when this lipoarabinomannan or lipid-free arabinomannan obtained by removing fatty acids from this lipoarabinomannan by saponification is chemically modified with a fatty acid, there is obtained chemically modified lipoarabinomannan which is comparable or superior to lipoarabinomannan extracted and purified from the cell body in the antitumor activity and has no side effect.

A culture of *Mycobacterium tuberculosis* strain Aoyama B has been deposited with the American Type Culture Collection, Rockville, Md. and added to its permanent collection as ATCC No. 31726. A culture of *Mycobacterium tuberculosis* Strain $H_{37}R_v$ has been deposited with the American Type Culture Collection, Rockville, Md. and added to its permanent collection as ATCC No. 25618.

DETAILED DESCRIPTION OF THE INVENTION

The components of the immunotherapeutic agent for tumors according to the present invention, the process for the preparation thereof and the therapeutic effects thereof will now be described in detail with reference to the following Examples and Experiments that by no means limit the scope of the invention.

EXAMPLE 1

In this Example, the process for extraction of the lipopolysaccharide is illustrated.

(1-1) Sauton culture medium is inoculated with *Mycobacterium tuberculosis* strain Aoyama B and aerobic culturing is conducted for 14 days. Cell body is recovered by filtration and washed with cold water, and distilled water is added to the cell body to float the cell body in water. The cell body dispersion is heated at 100° C. for 120 minutes and filtered to obtain an aqueous solution of the cell body extract. Sulfosalicyclic acid is added to the solution to precipitate the protein component and the solution is separated by centrifugal separation. The supernatant is dialyzed by using a dialysis membrane and the internal liquid is mixed with ethyl alcohol in an amount 9 times by volume as large as the amount of the internal liquid, and the mixture is separated by centrifugal separation and the precipitated crude lipopolysaccharide is recovered.

The crude lipopolysaccharide is dissolved in distilled water and mixed with the equal amount of ethyl alcohol, and the mixture is separated by centrifugal separation. The supernatant is concentrated and is sieved by molecular sieving according to high performance liquid chromatography using a column packed with TSK Gel 4000 Sw, TSK Gel 3000 SW and TSK Gel 2000 SW, each being a product supplied by Toyo Soda K.K., and a fraction of molecular weight of 10,000 to 16,000 is collected. The fraction is dialyzed and concentrated and further purified by affinity chromatography using agarosebead-concanavalin A supplied by E. Y. Laboratories to obtain a purified lipopolysaccharide.

(1-2) Mycobacterium tuberculosis strain $H_{37}Rv$ is cultured under the same conditions as disclosed in Example 1-1. The recovered cell body is treated by the same treatments as disclosed in Example 1-1 to obtain a crude lipopolysaccharide, which is purified through the same methods as disclosed in Example 1-1 into a purified lipopolysaccharide.

EXPERIMENT 1

Analysis of monosaccharide components of the lipopolysaccharide will now be described.

(1-1) The purified lipopolysaccharide obtained in Example 1-1 is hydrolyzed with sulfuric acid, neutralized with Amberlite 1R-45 (hydroxyl form) and identified by thin layer chromatography. Arabinose, mannose and glucose (arabinose:mannose:glucose=6:4:trace) are detected. The product obtained above by hydrolysis and neutralization is reduced and acetylated according to known methods, and the resulting alditol acetate mixture is determined by as chromatography using three kinds of packed column. It is confirmed that the mixture consists of 61% of arabinose, 38% of mannose and 1% of glucose. Thus, it is confirmed that the saccharide component of this lipopolysaccharide is arabinomannan.

(1-2) Monosaccharide components of the purified lipopolysaccharide obtained in Example 1-2 is analyzed by the same methods as disclosed in Experiment 1-1. As a result, it is confirmed that the refined sample consists of 56% of arabinose and 44% of mannose. Thus, it is confirmed that the saccharide component of this lipopolysaccharide is arabinomannan.

EXPERIMENT 2

Analysis of the saccharide chain structure of the lipopolysaccharide will now be described.

(2-1) The purified lipopolysaccharide obtained in Example 1-1 is completely methylated according to the Hakomori method, and the methylated lipopolysaccharide is hydrolyzed with sulfuric acid, neutralized with Amberlite 1R-45 (hydroxyl form) and reduced and acetylated according to known methods. The resulting partially methylated alditol acetate mixture is determined by gas chromatography using four kinds of packed column and SCOT capillary column. The detected peaks are compared with peaks of standard partially methylated alditol acetates synthesized separately, and the respective partially methylated saccharide components are identified and determined. Further, the respective saccharide components are confirmed and identified from pieces of the respective peaks by GC-MS.

The quantitative relation is partially methylated alditol acetate determined by gas chromatography and the linkages indicated are shown in Table 1.

(2-2) The purified lipopolysaccharide obtained in Example 1-2 is treated by the same treatments as disclosed in Experiment 2-1. The quantitative relation of partially methylated alditol acetate determined by gas chromatography and the linkages indicated are shown in Table 2.

EXPERIMENT 3

Analysis of fatty acids in the lipopolysaccharide will now be described.

(3-1) To 1 mg of the purified lipopolysaccharide obtained in Example 1-1 is added 1 ml of methyl alcohol containing 100 μg of methyl laurate as the internal standard and 3.3% of hydrogen chloride, and the mixture is decomposed by methanolysis in a sealed tube filled with nitrogen gas. The resulting mixture is concentrated at low temperature and dissolved in methylene chloride. By gas chromatography using two kinds of packed column, the constituent fatty acids are identified and determined by the retention time of the standard fatty acid methyl ester. The peaks of the respective fatty acid methyl esters are identified by GC-MS.

Results of the identification by gas chromatography are shown in Table 3.

TABLE 3

| | | |
|---|---|---|
| Methyl laurate (internal standard) | (100 μg) | |
| Methyl myristate | 10.4 μg | $42.9 \times 10^{-9}$ mol |
| Methyl palmitate | 89.5 μg | $330.9 \times 10^{-9}$ mol |
| Methyl heptadecanoate | 0.5 μg | $1.8 \times 10^{-9}$ mol |
| Methyl stearate | 37.3 μg | $125.0 \times 10^{-9}$ mol |
| Methyl oleate | 0.2 μg | $0.7 \times 10^{-9}$ mol |
| Methyl tuberculostearate | 12.8 μg | $41.0 \times 10^{-9}$ mol |
| Total | 150.7 μg | $542.3 \times 10^{-9}$ mol |

From the above experimental results, it is confirmed that the fatty acid content of the lipopolysaccharide sample is about 15% (150.7 μg per 1 mg polysaccharide) and it is suggested that the lipopolysaccharide (average molecular weight 13,000) which has been obtained in Example 1-1 contains about 7.6 fatty acids (1950 grams equivalent).

(3-2) The purified lipopolysaccharide obtained in Example 1-2 is treated by the same treatments as disclosed in Example 3-1 so as to identify and determine the constituent fatty acids. Results of the identification are shown in Table 4.

TABLE 1

| Detected Saccharide | Linkage Indicated | Ratio to 2-O—Methyl-Arabinose (= 1.0) | % | Remarks |
|---|---|---|---|---|
| 2,3,5-tri-O—methyl-D-arabinose | (Araf)1 → | 1.2 | 6.2 | |
| 2,3-di-O—methyl-D-arabinose | → 5(Araf)1 → | 8.0 | 41.0 | |
| 3,5-di-O—methyl-D-arabinose | → 2(Araf)1 → | 1.4 | 7.2 | 59.5% |
| 2-O—methyl-D-arabinose | →³₅(Araf)1 → | 1.0 | 5.1 | |
| 2,3,4,6-tetra-O—methyl-D-mannose | (Manp)1 → | 2.5 | 12.8 | |
| 3,4,6-tri-O—methyl-D-mannose | → 2(Manp)1 → | 1.2 | 6.1 | |
| 2,3,4-tri-O—methyl-D-mannose | → 6(Manp)1 → | 1.4 | 7.2 | 40.5% |
| 3,4-di-O—methyl-D-mannose | →²₆(Manp)1 → | 2.8 | 14.4 | |
| Total | | 19.5 | 100 | |

TABLE 2

| Detected Saccharide | Linkage Indicated | Ratio to 2-O—Methyl-Arabinose (= 1.0) | % | Remarks |
|---|---|---|---|---|
| 2,3,5-tri-O—methyl-D-arabinose | (Araf)1 → | 0.9 | 3.0 | |
| 2,3-di-O—methyl-D-arabinose | → 5(Araf)1 → | 12.4 | 41.5 | |
| 3,5-di-O—methyl-D-arabinose | → 2(Araf)1 → | 2.3 | 7.7 | 55.5% |
| 2-O—methyl-D-arabinose | →³₅(Araf)1 → | 1.0 | 3.3 | |
| 2,3,4,6-tetra-O—methyl-D-mannose | (Manp)1 → | 2.8 | 9.4 | |
| 3,4,6-tri-O—methyl-D-mannose | → 2(Manp)1 → | 2.7 | 9.0 | |
| 2,3,4-tri-O—methyl-D-mannose | → 6(Manp)1 → | 5.3 | 17.7 | 44.5% |
| 3,4-di-O—methyl-D-mannose | →²₆(Manp)1 → | 2.5 | 8.4 | |
| Total | | 29.9 | 100 | |

TABLE 4

| | | |
|---|---|---|
| Methyl laurate (internal standard) | (100 µg) | |
| Methyl myristate | 6.6 µg | $27.2 \times 10^{-9}$ mol |
| Methyl palmitate | 39.6 µg | $146.4 \times 10^{-9}$ mol |
| Methyl heptadecanoate | 0.4 µg | $1.4 \times 10^{-9}$ mol |
| Methyl stearate | 13.2 µg | $44.2 \times 10^{-9}$ mol |
| Methyl tuberculostearate | 19.8 µg | $63.4 \times 10^{-9}$ mol |
| Total | 79.6 µg | $282.6 \times 10^{-9}$ mol |

From the above experimental results, it is confirmed that the fatty acid content of the lipopolysaccharide sample is about 8% (79.6 µg per 1 mg polysaccharide) and it is suggested that the lipopolysaccharide (average molecular weight 12,000) which has been obtained in Example 1-2 contains about 3.9 fatty acids (1,000 grams equivalent).

EXPERIMENT 4

Analysis of the fatty acid linkage structure of the lipopolysaccharide will now be described.

(4-1) The purified lipopolysaccharide obtained in Example 1-1 is treated with methylvinyl ether in dimethylsulfoxide in the presence of p-toluene-sulfonic acid as a catalyst to methoxyethylate free hydroxyl groups. The fatty acids are removed by saponification and the hydroxyl groups which have been set free are methylated according to the Hakomori method. Then, the methoxyethyl groups are removed by hydrolysis using an acid containing methyl alcohol, and partially methylated monosaccharide mixture is obtained by hydrolysis with an acid. The mixture is reduced and acetylated according to the known methods, and the acetates are analyzed by gas chromatography using three kinds of packed column and xylitol as an internal standard and identification and determination are carried out by comparison with standard alditol acetates of free and partially methylated monosaccharides.

Identified peaks are as shown in Table 5.

TABLE 5

| | | | |
|---|---|---|---|
| 5-methyl-D-arabinitol | 6.14% | | |
| 2-methyl-D-arabinitol | 2.48% | | |
| 3-methyl-D-arabinitol | 0.33% | } | 59.22% |
| D-arabinitol | 50.27% | | |
| 2-methyl-D-mannitol | 0.02% | | |
| 3- or 4-methyl-D-mannitol | 0.22% | | |
| 6-methyl-D-mannitol | 1.04% | } | 40.78% |
| D-mannitol | 39.50% | | |
| Total | 100% | | (including 10.23% of fatty acid ester of monosaccharide) |

From the above experimental results, it is suggested that about one fatty acid is bonded per 10 molecules of the constituent monosaccharides, and most of the bonding positions are the 5-positions of arabinose units and the rest are the 2-positions of arabinose units, the 6-positions of mannose units and other positions.

From the analysis results obtained in Experiments 1-1, 2-1, 3-1 and 4-1, it is expected that the lipopolysaccharide obtained in Example 1-1 is a lipopolysaccharide having an average molecular weight of about 13,000, which consists of arabinomannan having an average molecular weight of about 11,000 composed of about 47 arabinose units and about 30 mannose units and about 8 fatty acids having 14 to 19 carbon atoms (palmitic acid in the main) which are bonded to the arabinomannan.

(4-2) The purified lipopolysaccharide obtained in Example 1-2 is treated by the same treatments as disclosed in Experiment 4-1. Peaks of the presulting partially methylated alditol acetate are identified as shown in Table 6.

TABLE 6

| | | | |
|---|---|---|---|
| 5-methyl-D-arabinitol | 3.29% | | |
| 2-methyl-D-arabinitol | 1.60% | | |
| 3-methyl-D-arabinitol | 0.03% | } | 55.49% |
| D-arabinitol | 50.57% | | |
| 2-methyl-D-mannitol | 0.01% | | |
| 3- or 4-methyl-D-mannitol | 0.03% | | |
| 6-methyl-D-mannitol | 1.00% | } | 44.51% |
| D-mannitol | 43.47% | | |
| Total | 100% | | (including 5.96% of fatty acid ester of monosaccharide) |

From the above experimental results, it is suggested that about one fatty acid is bonded per 16 molecules of the constituent monosaccharides, and most of the bonding positions are the 5- and 2-positions of arabinose units and the 6-positions of mannose units.

From the analysis results obtained in Experiments 1-2, 2-2, 3-2 and 4-2, it is expected that the lipopolysaccharide obtained in Example 1-2 is a lipopolysaccharide having average molecular weight of about 12,000, which consists of arabinomannan having average molecular weight of about 11,000 composed of about 42 arabinose units and about 34 mannose units and on an average 4 or 5 fatty acids having 14 to 19 carbon atoms (palmitic acid in the main) which are bonded to the arabinomannan.

A process for obtaining a lipopolysaccharide by bonding a fatty acid to a polysaccharide is known. According to the present invention, lipoarabinomannan more effective for the immunotherapy of tumors can be prepared by bonding an appropriate fatty acid to lipid-free or low-lipid arabinomannan by this known process.

EXAMPLE 2

This example illustrates the process of preparing lipoarabinomannan from lipid-free arabinomannan.

(2-1) The cell body used in Example 1-1 is alkali-extracted and arabinomannan having molecular weight of about 8,500 to 14,000 is obtained by molecular sieving in the same manner as described in Example 1-1. The so obtained arabinomannan is further refined by affinity chromatography and dried and 10 mg of the dried arabinomannan is reacted with 10 mg of palmitic anhydride at 50° C. for 20 hours in N,N-dimethylformamidepyridine. Ethyl ether is added to the reaction mixture and the precipitate is recovered by centrifugal separation, washed with ethyl ether and dried to obtain 11 mg of lipoarabinomannan.

As the result of the analysis, it has been confirmed that the saccharide chain structure of the above obtained lipoarabinomannan is substantially the same as that detected in Experiments 1-1 and 2-1. More specifically, it has been confirmed that palmitic acid is bonded mainly to the 5-position of the arabinose unit in the arabinomannan chain in an amount of about 9.8% by weight and the average molecular weight is about 12,500.

(2-2) The cell body used in Example 1-2 is alkali-extracted and arabinomannan is obtained and refined in the same manner as described in Example 2-1. 10 mg of the dried arabinomannan is reacted with 8 mg of palmitoyl chloride at 37° C. for 16 hours in N,N-dimethylformamide-pyridine. Ethanol is added to the reaction mixture and the precipitate is recovered by centrifugal separation, washed with ethyl ether and dried to obtain 10 mg of lipoarabinomannan.

As the result of the analysis, it has been confirmed that the saccharide chain structure of the above obtained lipoarabinomannan is substantially the same as that detected in Experiments 1-2 and 2-2. More specifically, it has been confirmed that palmitic acid is bonded mainly to the 5-position of the arabinose unit in the arabinomannan chain in an amount of about 7.6% by weight and the average molecular weight is about 12,000.

EXAMPLE 3

This Example illustrates the process of preparing lipoarabinomannan from low-lipid arabinomannan.

(3-1) 5 mg of arabinomannan having fatty acid content of about 3%, which has been obtained in the same manner as described in Example 1-1 is ultrasonically treated with 10 mg of palmitoyl chloride in pyridine and reaction is carried out at 37° C. for 18 hours. Ethyl alcohol is added to the reaction mixture and the precipitate is collected, washed with ethyl ether and dried to obtain 4.3 mg of lipoarabinomannan.

As the result of the analysis, it has been confirmed that the saccharide chain structure is substantially the same as that detected in Experiments 1-1 and 2-1. More specifically, it has been confirmed that palmitic acid is bonded mainly to the 5-position of the arabinose unit and the 6-position of the mannose unit in the arabinomannan chain in an amount of about 28% by weight and the average molecular weight is about 14,000.

(3-2) 5 mg of arabinomannan having fatty acid content of about 2%, which has been obtained in the same manner as described in Example 1-2 is ultrasonically treated with 8 mg of palmitoyl chloride in pyridine and reaction is carried out at 37° C. for 18 hours. Ethyl alcohol is added to the reaction mixture and the precipitate is collected, washed with ethyl ether and dried to obtain 3.8 mg of lipoarabinomannan.

As the result of the analysis, it has been confirmed that the saccharide chain structure is substantially the same as that detected in Experiments 1-2 and 2-2. More specifically, it has been confirmed that palmitic acid is bonded mainly to the 5-position of the arabinose unit and the 6-position of the mannose unit in the arabinomannan chain in an amount of about 18% by weight and the average molecular weight is about 13,500.

Stearic acid may be employed instead of palmitic acid in Example 2 or 3.

EXPERIMENT 5

In this Experiment, the anti-tumor activity is tested. Cells ($1 \times 10^6$) of Sarcoma-180 tumor are subcutaneously transplanted on ddY mice (female, 10 weeks old) which have been sensitized by BCG. Since the next day, lipoarabinomannan indicated in Table 7, which is sterilely dissolved in a physiological saline is hypodermically administered to groups of mice (each group consisting of 8 mice) in an amount of 0.02 μg to 2.0 μg per mouse every other day 8 times as a whole. When 30 days have passed after the transplantation of the tumor cells, the test animals are killed and the tumor weights are measured. The anti-tumor activity of each lipoarabinomannan is evaluated based on the measured tumor weight.

The obtained results are shown in Table 7.

TABLE 7

| Group | Amount Administered (μg) | Tumor Weight ± S.E. (g) | T/C (%) |
|---|---|---|---|
| Control | — | 2.71 ± 0.32 | 100 |
| ArMn-1[a] | 0.02 | 2.54 ± 0.43 | 93.7 |
| " | 0.2 | 1.78 ± 0.26* | 65.7 |
| " | 2.0 | 1.70 ± 0.29* | 62.7 |
| Control | — | 2.82 ± 0.40 | 100 |
| ArMn-2[b] | 0.02 | 1.90 ± 0.52 | 67.4 |
| " | 0.2 | 1.62 ± 0.24** | 57.4 |
| " | 2.0 | 1.74 ± 0.25** | 61.7 |
| Control | — | 2.53 ± 0.33 | 100 |
| ArMn-3[c] | 0.02 | 1.87 ± 0.40 | 73.9 |
| " | 0.2 | 1.53 ± 0.27* | 60.5 |
| " | 2.0 | 1.54 ± 0.27* | 60.9 |
| Control | — | 2.85 ± 0.21 | 100 |
| ArMn-4[d] | 0.02 | 1.52 ± 0.82** | 53.3 |
| " | 0.2 | 1.40 ± 0.15** | 49.1 |
| " | 2.0 | 1.83 ± 0.17** | 64.2 |
| Control | — | 3.24 ± 0.46 | 100 |
| ArMn-5[e] | 0.02 | 2.21 ± 0.22** | 68.2 |
| " | 0.2 | 1.63 ± 0.21** | 50.3 |
| " | 2.0 | 1.77 ± 0.24** | 54.6 |
| Control | — | 3.12 ± 0.32 | 100 |
| ArMn-6[f] | 0.02 | 1.95 ± 0.19** | 62.5 |
| " | 0.2 | 1.51 ± 0.14** | 48.4 |
| " | 2.0 | 1.80 ± 0.20** | 57.7 |
| Control | — | 3.35 ± 0.34 | 100 |
| ArMn-7[g] | 0.02 | 2.34 ± 0.22** | 69.9 |
| " | 0.2 | 1.49 ± 0.36** | 44.8 |
| " | 2.0 | 1.67 ± 0.34** | 49.9 |

Note
[a] Lipoarabinomannan extracted and purified by the process described in Example 1-1 (fatty acid content = 3%)
[b] Lipoarabinomannan extracted and purified in Example 1-1 (fatty acid content = 15%)
[c] Lipoarabinomannan formed by bonding palmitic acid to lipid-free arabinomannan through an ester linkage in Example 2-1 (palmitic acid content = 10%)
[d] Lipoarabinomannan formed by bonding palmitic acid to low-lipid lipoarabinomannan through an ester linkage in Example 3-1 (palmitic acid content = 28%)
[e] Lipoarabinomannan extracted and purified in Example 1-2 (fatty acid content = 8%)
[f] Lipoarabinomannan formed by bonding palmitic acid to lipid-free arabinomannan through an ester linkage in Example 2-2 (palmitic acid content = 7.6%)
[g] Lipoarabinomannan formed by bonding palmitic acid to low-lipid lipoarabinomannan through an ester linkage in Example 3-2 (palmitic acid content = 18%)
T/C (%): the ratio of the tumor weight in the lipopolysaccharide-administered group to the tumor weight in the control group
*$P < 0.05$
**$P < 0.01$ As will be apparent from the results shown in Table 7 the lipopolysaccharides of the present invention, that is, both the lipoarabinomannan formed by bonding a fatty acid to lipid-free or low-lipid arabinomannan and the lipoarabinomannan extracted and purified from the cell body, have a high inhibitory effect to growth of the tumor with small amount administered. The arabinomannan having a larger fatty acid content has an especially high anti-tumor effect with less amount administered.

When the lipopolysaccharide of the present invention is administered as an immunotherapeutic agent for tumors, it is formed into a hypodermic injection. An example of the preparation of a hypodermic injection will now be described.

EXAMPLE 4

1 mg of lipopolysaccharide of the present invention (obtained in Example 1, 2 or 3) is dissolved in an appropriate amount of a physiological saline for injection to form 100 ml of a solution. The solution is prepared into a hypodermic injection containing 10 82 g/ml of the lipopolysaccharide according to customary procedures. The injection is hypodermically administered 1 to 3 times (10 to 30 μg as lipopolysaccharide) a week.

The cell body of tubercle bacillus or extract thereof, anti-tumor activity of which has been evaluated, is a mixture of complicated chemical components. In contrast, the lipoarabinomannan of the present invention is a lipopolysaccharide having definite chemical composition, which is isolated and purified. Furthermore, the lipopolysaccharide of the present invention is characterized in that side effects possessed by the cell body can be eliminated. Accordingly, it is expected that the lipopolysaccharide of the present invention will be a valuable immunotherapeutic agent for tumors.

What is claimed is:

1. An immunotherapeutic agent for tumors, which comprises as an effective component lipopolysaccharide comprising, arabinomannan as a polysaccharide and fatty acids bonded to said arabinomannan through an ester linkage, the fatty acid content in said lipopolysaccharide being 3 to 28%, said lipopolysaccharide being obtained by hot water extraction and purification of the cell body of human tubercle bacillus, *Mycobacterium tuberculosis* strain Aoyama B or *Mycobacterium tuberculosis* strain $H_{37}R_v$.

2. An immunotherapeutic agent for tumors, which comprises as an effective component lipopolysaccharide prepared by bonding a fatty acid to arabinomannan through an ester linkage, said arabinomannan being obtained by alkali extraction and purification of the cell body of human tubercle bacillus, *Mycobacterium tuberculosis* strain Aoyama B or *Mycobacterium tuberculosis* strain $H_{37}R_v$, the fatty acid content in said lipopolysaccharide being 3 to 28%.

3. An immunotherapeutic agent for tumors, which comprises as an effective component lipopolysaccharide prepared by bonding a fatty acid to lipoarabinomannan through an ester linkage, said lipoarabinomannan being obtained by hot water extraction and purification of the cell body of human tubercle bacillus, *Mycobacterium tuberculosis* strain Aoyama B or *Mycobacterium tuberculosis* strain $H_{37}R_v$, the fatty acid content in said lipopolysaccharide being 3 to 28%.

4. An immunotherapeutic agent for tumors according to claim 1 wherein said fatty acids are palmitic acid, myristic acid, stearic acid, tuberculostearic acid, heptadecanoic acid, oleic acid and linoleic acid and said lipopolysaccharide has a monosaccharide composition of 30 to 74% of arabinose, 20 to 50% of mannose, 0 to 10% of glucose and 0 to 13% of galactose.

5. An immunotherapeutic agent for tumors according to claim 2 or 3 wherein fatty acid is selected from the group consisting of palmitic acid and stearic acid and said lipopolysaccharide has a monosaccharide composition of 30 to 74% of arabinose, 20 to 50% of mannose, 0 to 10% of glucose and 0 to 13% of galactose.

* * * * *